(12) United States Patent
Kim et al.

(10) Patent No.: US 8,257,503 B2
(45) Date of Patent: Sep. 4, 2012

(54) METHOD AND APPARATUS FOR DETECTING PLASMA UNCONFINEMENT

(75) Inventors: KeeChan Kim, Pleasanton, CA (US); Yunsang Kim, San Jose, CA (US); Andrew D. Bailey, III, Pleasanton, CA (US)

(73) Assignee: Lam Research Corporation, Fremont, CA (US)

( * ) Notice: Subject to any disclaimer, the term of this patent is extended or adjusted under 35 U.S.C. 154(b) by 619 days.

(21) Appl. No.: 12/114,681

(22) Filed: May 2, 2008

(65) Prior Publication Data
US 2009/0272402 A1 Nov. 5, 2009

(51) Int. Cl.
*C25F 3/30* (2006.01)
(52) U.S. Cl. .......................... 134/1.3; 134/1.1
(58) Field of Classification Search .................. None
See application file for complete search history.

(56) References Cited

U.S. PATENT DOCUMENTS

| | | | | |
|---|---|---|---|---|
| 5,759,424 A | * | 6/1998 | Imatake et al. | 216/60 |
| 5,980,767 A | * | 11/1999 | Koshimizu et al. | 216/60 |
| 2007/0068623 A1 | * | 3/2007 | Kim et al. | 156/345.3 |
| 2007/0068900 A1 | * | 3/2007 | Kim et al. | 216/67 |

\* cited by examiner

*Primary Examiner* — Michael Kornakov
*Assistant Examiner* — Nicole Blan
(74) *Attorney, Agent, or Firm* — Martine Penilla Group LLP

(57) ABSTRACT

A method for detecting plasma unconfinement in a reaction chamber during a bevel edge cleaning operation is provided. The method initiates with selecting a wavelength associated with expected by products of a bevel edge clean process. The method includes cleaning the bevel edge area of a substrate and monitoring the intensity of the selected wavelengths during the cleaning for deviation from a threshold wavelength intensity. The cleaning is terminated if the deviation from the threshold wavelength intensity exceeds a target deviation.

18 Claims, 4 Drawing Sheets

METHOD AND APPARATUS FOR DETECTING PLASMA UNCONFINEMENT

BACKGROUND

As feature sizes are becoming smaller and smaller, the cleaning of the edge region of the wafer is becoming more difficult. In addition, as newer cleaning techniques are being adapted for the manufacturing process to achieve the smaller feature sizes, there are different process chemistries being utilized for these techniques. Some of these processing chemistries may be corrosive to the active portion of the wafer, i.e., the region of the wafer where the integrated circuits are defined. Another consequence of the shrinking feature sizes is that the edge exclusion zone is becoming smaller. Thus, any cleaning of the edge must be directed to the edge so that the corrosive chemistries do not impact the remainder of the wafer. Currently, techniques are being developed in order to facilitate the cleaning of the edge so that any particulates or contamination can be removed from the processing performed on the substrate. However, there is a need to be able to clean the edge without affecting the center portion of the wafer. As new processes are being used for wafer processing, this need will become more apparent, especially with the use of corrosive processing gases as cleaning chemistries.

Currently when cleaning wafers or the bevel edges of a wafer, the cleaning process is manually controlled. That is, visual inspection of the process through a process window alerts an operator that the plasma used to clean the bevel edge has become unconfined and may affect the actual integrated circuits on the semiconductor substrate. The use of a visual inspection of the process when using a plasma to clean the bevel edge yields unreliable results.

In view of the foregoing, there is a need for systems and methods to reliably monitor the confinement of a plasma when cleaning a bevel edge of a wafer in order to reliably monitor the confinement of the plasma.

SUMMARY

Broadly speaking, the present invention fills these needs by providing an improved cleaning technique and cleaning solution. It should be appreciated that the present invention can be implemented in numerous ways, including as a system, an apparatus and a method. Several inventive embodiments of the present invention are described below.

In one embodiment, a method for detecting plasma unconfinement in a reaction chamber during a bevel edge cleaning operation is provided. The method initiates with selecting a wavelength associated with expected by products of a bevel edge clean process. The method includes cleaning the bevel edge area of a substrate and monitoring the selected wavelengths during the cleaning for deviation from a wavelength intensity. The cleaning is terminated if the deviation from the wavelength intensity exceeds a target deviation.

In another embodiment, a method for preventing plasma unconfinement in a reaction chamber during an edge cleaning process is provided. The method initiates with processing a semiconductor substrate in a processing chamber. The processing deposits by products on a peripheral edge of the substrate. The method includes performing an edge cleaning process to remove the deposited by products. The edge cleaning process includes striking a plasma confined to the peripheral edge region of the substrate and monitoring confinement of the plasma to the peripheral edge region. The monitoring includes tracking a wavelength signal during the edge cleaning process and determining whether the plasma remains confined based on fluctuation of the tracked wavelength signal.

Other aspects and advantages of the invention will become more apparent from the following detailed description, taken in conjunction with the accompanying drawings, illustrating by way of example the present invention.

BRIEF DESCRIPTION OF THE DRAWINGS

The present invention will be readily understood by the following detailed description in conjunction with the accompanying drawings, and like reference numerals designate like structural elements.

DETAILED DESCRIPTION

In the following description, numerous specific details are set forth in order to provide a thorough understanding of the present invention. It will be apparent, however, to one skilled in the art that the present invention may be practiced without some or all of these specific details. In other instances, well known process operations have not been described in detail in order not to unnecessarily obscure the present invention.

The embodiments described herein provide a system and method to monitor the confinement of a plasma used to clean a bevel edge region of a substrate. In one embodiment, the optical emission spectrometry (OES) monitors a selected wavelength dependent on the material being cleaned from the bevel area of the wafers. As will be illustrated in the embodiments described below, the intensity of the monitored wavelength will remain stable during the cleaning time as long as the plasma remains confined. Should the plasma go unconfined, then the intensity of the wavelength being monitored will fluctuate.

Figure 1:
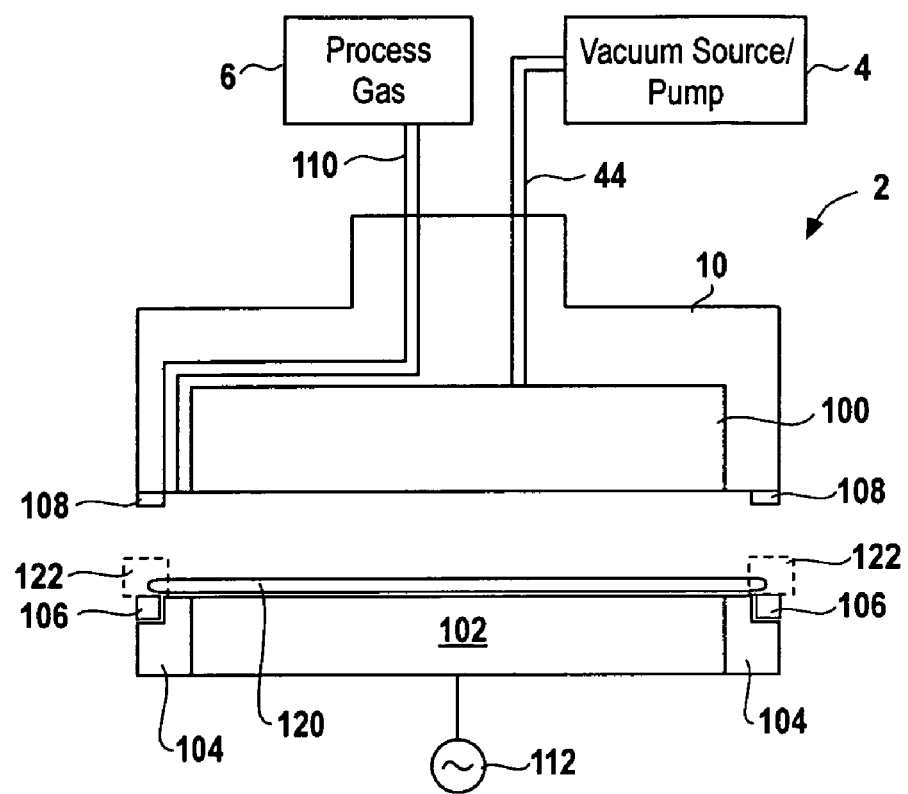
FIG. 1 is a simplified schematic diagram illustrating an exemplary cross sectional view of a processing chamber in accordance with one embodiment of the invention.

FIG. 1 is a simplified schematic diagram illustrating an exemplary cross sectional view of a processing chamber in accordance with one embodiment of the invention. In one embodiment, the processing chamber described herein is a bevel edge etching system where gas may be fed from various regions in order to etch the edge of a substrate or wafer disposed within the chamber. The etching of the edge region cleans this area from byproducts disposed thereon. Bevel etch chamber 2 includes a channel 44 through a center region of an upper electrode assembly 10 of the chamber top and allows access into the reaction chamber where a wafer is processed. Channel 44 is connected at one end to vacuum source/pump 4. Reaction chamber 2 includes top insulator block 100 disposed over bottom electrode 102, which is powered by radio frequency (RF) generator 112. It should be noted that bottom electrode 102 may also be referred to as a powered substrate support. Gas supply 110 will supply gas to a region proximate to the edge of wafer 120 from process gas supply 6. Top ground electrode 108 is disposed over a peripheral edge region of wafer 120, i.e., the bevel edge region of the wafer. Bottom ground electrode 106 is disposed under an edge region of wafer 120 and opposes top electrode 108. It should be appreciated that bottom electrode 106 and top electrode 108 are grounded in one embodiment. Dielectric 104 electrically isolates bottom electrode 106 from powered substrate support 102. Of course, electrodes 106 and 108 may be powered in another embodiment. Within region 122, a plasma is struck between electrodes 108 and 106. One skilled in the art will appreciate that by applying a vacuum source, or a pump to pump out from channel 44, the pressure gradient within reaction chamber 2 may be adjusted during the cleaning of the bevel edge.

While FIG. 1 illustrates the entry of the process gas in a location proximate to plasma region 122, the embodiments are not limited to this configuration. That is, the process gas can be introduced anywhere between an inner surface of electrode 108 and channel 44. One skilled in the art will appreciate that changing the entry location of the process gas through the top of the chamber, the pressure profile experienced by the substrate may be manipulated. In an alternative embodiment, an inert gas may be pumped through center feed/channel 44 of chamber 2 while a process gas is delivered to the outer periphery or edge region of the chamber which is proximate to the bevel edge of the wafer. Thus, the plasma would be struck in the edge region while the etch process gas is flowing proximate to the outer periphery and the inert gas flows into the center region. The flow rate of the inert gas in the center region may be used to manipulate a pressure experienced by the wafer similar to the pump out procedure described herein. Through the embodiments described herein, one exemplary pressure gradient may be defined as the center region of the wafer experiencing a pressure of about 50 TORR, while the outer edge of the wafer is exposed to a pressure of about 2 TORR. Of course, this range can be reversed through the embodiments described above as channel 44 may be used to supply a gas to increase the pressure or channel 44 may be used to pump out the region of the chamber to reduce the pressure. One skilled in the art will appreciate that the distance from a top surface of wafer 122 and the bottom of insulator block 100 is about 4 mm in one embodiment, thus allowing the pressure gradient to exist. Further information on the gas distribution for the bevel edge etcher may be found in U.S. patent application Ser. No. 11/697,695, which is incorporated herein by reference for all purposes.

Figure 2:
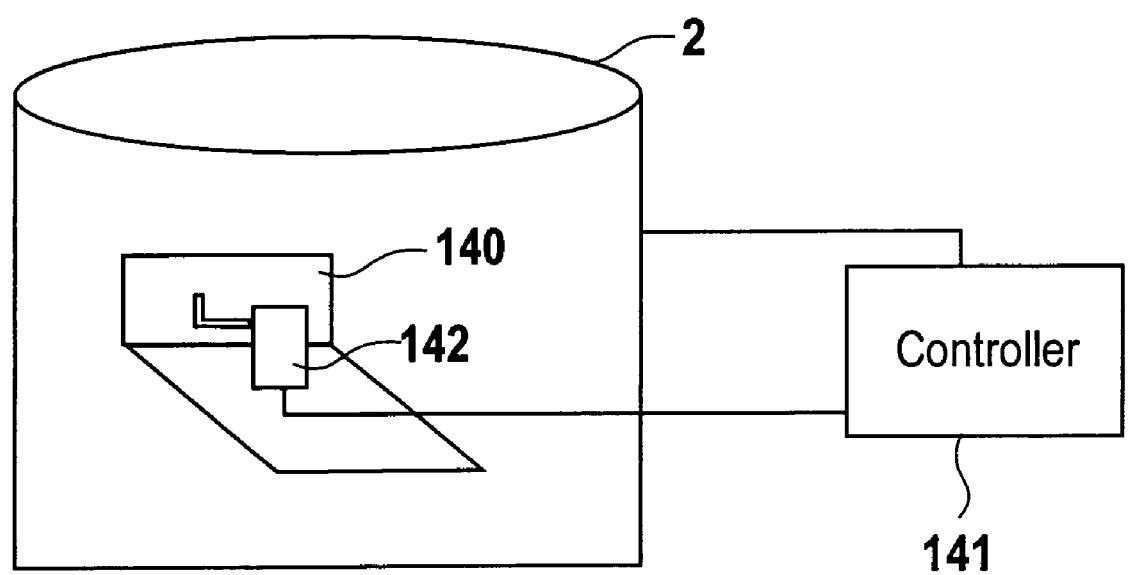
FIG. 2 is a simplified schematic diagram illustrating a side view of a chamber having a window through which the wavelength may be monitored in accordance with one embodiment of the invention.

FIG. 2 is a simplified schematic diagram illustrating a side view of a chamber having a window through which the wavelength may be monitored in accordance with one embodiment of the invention. Chamber 2 includes window 140 that enables access for monitoring a wavelength within region 122 of FIG. 1 being processed inside chamber 2. Region 122 represents the plasma region in accordance with one embodiment of the invention. OES signal monitor 142 may rest on a platform off of chamber 2 and is configured to monitor a wavelength intensity in region 122 through window 140. In one embodiment, window 140 is a quartz window. In another embodiment, the sensor for OES signal monitor 142 is integrated into chamber 2, e.g., embedded into a sidewall, and monitors the process in this manner. With regard to a $CF_4$ based chemistry used to etch silicon dioxide wafers, the byproducts from the bevel clean process, i.e., SiF and CO may be selected for the wavelength signals to be monitored. Controller 141 is in communication with OES signal monitor 142 and chamber 2. Thus, from the monitoring of the respective wavelengths during the bevel etch cleaning process, the controller can detect an unconfined condition for the plasma and terminate the process, thereby preventing the integrated circuits defined on the substrate from becoming damaged.

Figure 3A:
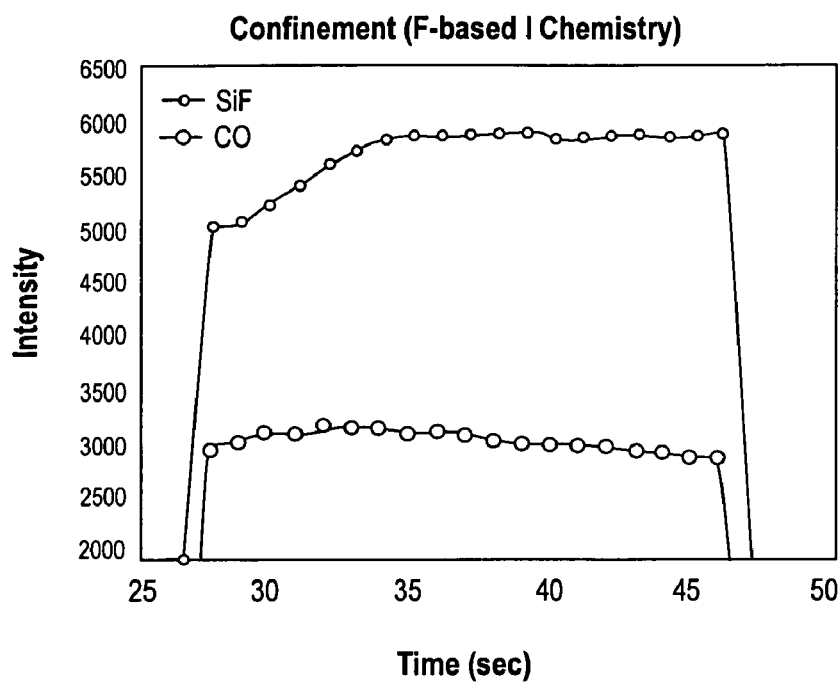
FIGS. 3A and 3B are exemplary graphical illustrations depicting intensity fluctuations during confined and unconfined plasma conditions in accordance with one embodiment of the invention.
Figure 3B:
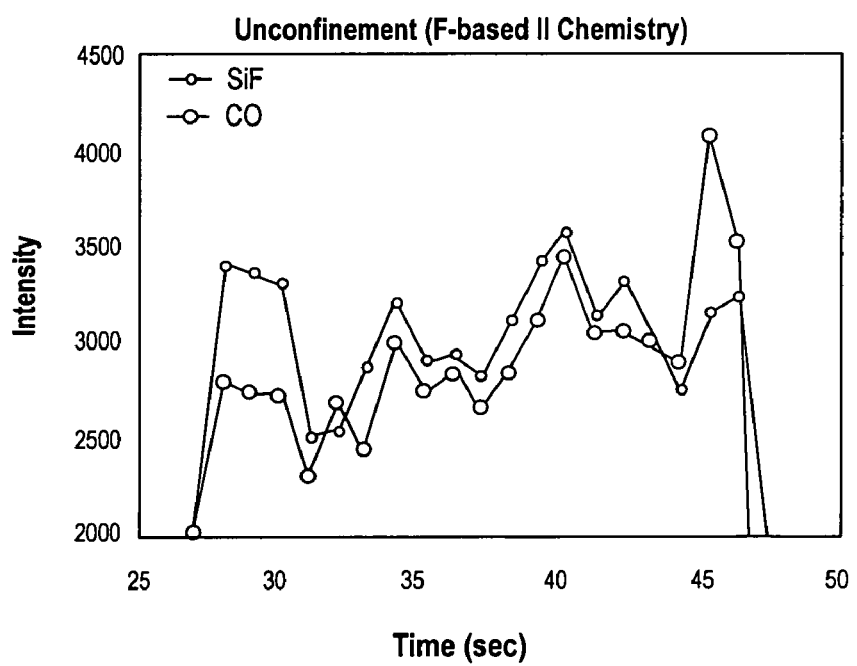

FIGS. 3A and 3B are exemplary graphical illustrations depicting intensity fluctuations during confined and unconfined plasma conditions in accordance with one embodiment of the invention. With regards to FIGS. 3A and 3B, it should be appreciated that in the case of plasma confinement as illustrated in FIG. 3A both signals steadily increase and saturate at a constant level. In contrast, as illustrated in FIG. 3B, the signals for the fluorine based chemistry will fluctuate when the plasma becomes unconfined. FIG. 3A represents a 17% change between the maximum minus the minimum divided by the average [(6100−5100)/5600] in the silicon fluoride reading while the carbon monoxide reading has an 8% maximum minus minimum over the average intensity in change [(2200−1950)/3050]. In contrast, the unconfined instance of FIG. 3 yields a 54% change in the silicon fluoride wavelength intensity and a 72% change in the carbon monoxide wavelength intensity. Thus, the output of the intensity may be tracked over time to determine the [(max−min)/avg]. This result can then be compared to a threshold level to determine whether an unconfined condition exists within the processing chamber. It should be appreciated that while FIGS. 3A and 3B refer to silicon fluoride and carbon monoxide for a fluorine based chemistry, other suitable by-product associated wavelengths for fluorine or non-fluorine based chemistries may be monitored to determine an unconfined condition as discussed herein. Table 1 below lists other possible by-products from corresponding materials being etched and the etch gases used.

TABLE 1

| Material | Etch gas | Etch by-products |
| --- | --- | --- |
| Si | $CF_4$, $SF_6$ | $SiF_4$ |
| $SiO_2$ | $CF_4$, $SF_6$ | $SiF_4$, CO |
| SiN | $CF_4$, $SF_6$ | $SiF_4$ |
| W, Ta, Ti | $SF_6$, $CF_4$ | $WF_6$, $TaF_6$, $TiF_6$ |
| Organic, C (Photoresist) | $O_2$, $O_2/CF_4$ | CO, $CO_2$, HF, $H_2$, $H_2O$ |

Figure 4:
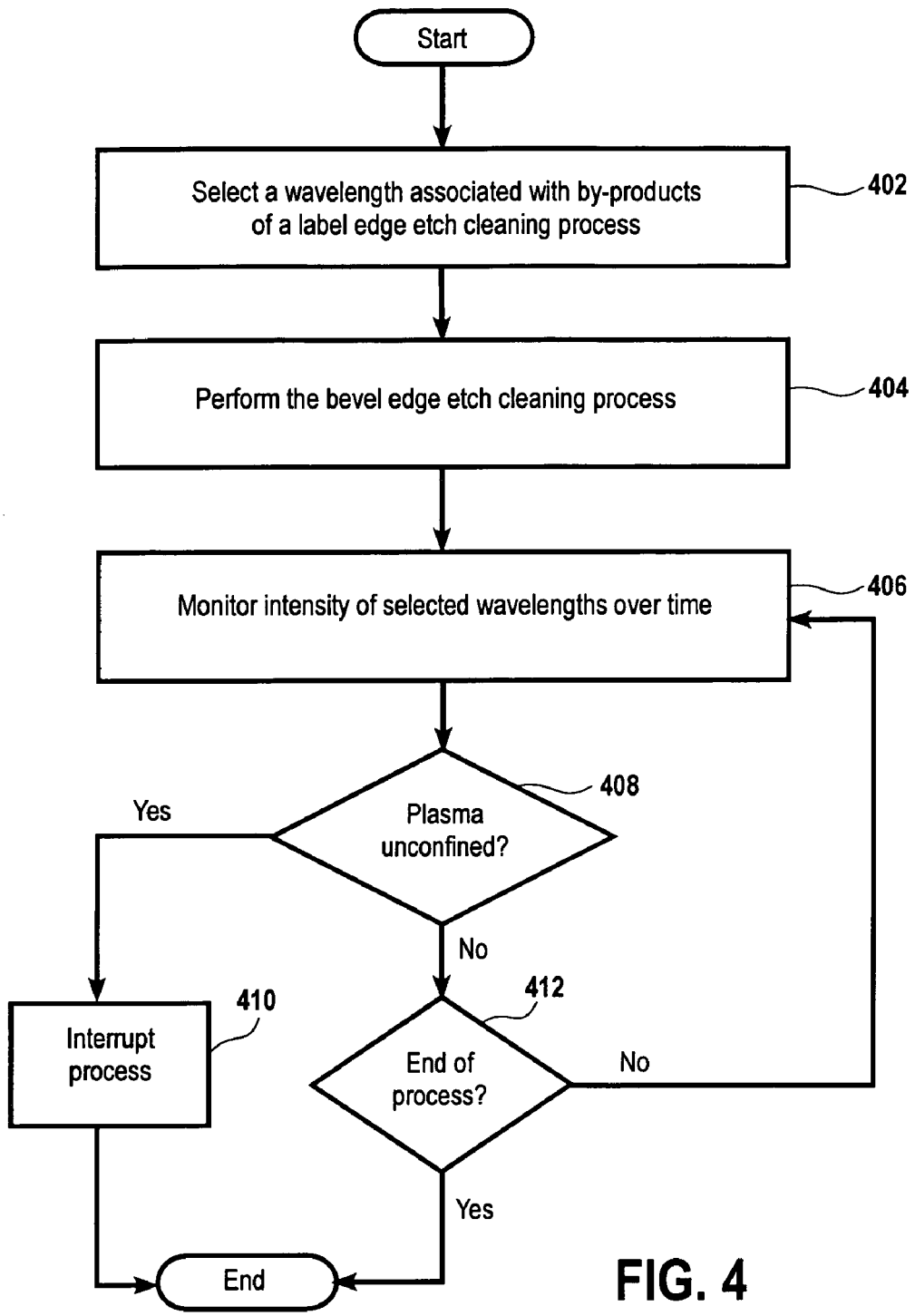
FIG. 4 is a simplified schematic diagram illustrating method operations for determining a plasma unconfinement in accordance with one embodiment of the invention.

FIG. 4 is a simplified schematic diagram illustrating method operations for determining a plasma unconfinement in accordance with one embodiment of the invention. The method initiates with operation 402 where a wavelength expected from the byproducts during the bevel clean process is selected. For example, with a fluorine based chemistry as illustrated in FIGS. 3A and 3B, the intensity of the silicon fluoride and carbon monoxide byproducts may be monitored. The method then advances to operation 404 where a process recipe is run to clean the bevel area of the wafers. In one embodiment, the chamber illustrated in FIGS. 1 and 2 may be utilized to create a plasma in a bevel edge region in order to clean the bevel area of the wafers. The method then moves to operation 406 where the selected wavelengths are monitored using an optical emission spectrometer as described above. The optical emission spectrometer may view the process through a window having access to the edge region of the substrate being processed, where the OES may be resting on a shelf proximate to the window and tied into a controller controlling the process operations within the chamber. In one embodiment, the OES, or a sensor of the OES, may be integrated into the chamber.

The method of FIG. 4 then advances to operation 408 where it is determined whether the plasma within the bevel edge area is confined or unconfined. If the plasma is confined, the method continues until the process operation for cleaning the bevel edge is completed. Of course, the determination of whether the plasma is confined may continually be performed throughout the cleaning process. If the method determines that the plasma is unconfined, the method advances to operation 410 where the process is interrupted in order to protect the wafer. The process can be re-started and the confinement remonitored upon any correction thereafter. It should be appreciated that the confinement will be determined based on a substantially steady or constant level of the intensity of the wavelength being monitored. That is, unconfined conditions may be detected when the intensity fluctuates from a threshold level as described above. If the plasma is confined for the time instance being monitored, the method advances to operation 412 where it is determined if the end of the process has been reached. If the end of the process has not been reached, the method returns to operation 406 and repeats as described above for another time instance. If the process has ended, then the method terminates.

The embodiments described above provide for detecting plasma confinement during a bevel edge plasma cleaning. By monitoring the intensity of wavelengths associated with the plasma generated for the bevel edge cleaning, and comparing the variation of the intensity to a threshold value, a decision to interrupt the process can be made in order to protect the integrated circuits on the substrate from unconfined plasma. As described above, an unconfined condition is detectable due to the a degree of fluctuation of the intensity. This degree of fluctuation is tracked by an OES unit and when the fluctuation is indicative of an unconfined condition, the process can be halted.

Although the present invention has been described in the context of removing contaminants from a semiconductor wafer, it should be understood that the previously described principles and techniques of the present invention can be equally applied to cleaning surfaces other than semiconductor wafers. For example, the present invention can be used to clean any equipment surface used in semiconductor manufacturing, wherein any equipment surface refers to any surface that is in environmental communication with the wafer, e.g., shares air space with the wafer. The present invention can also be used in other technology areas where contamination removal is important. For example, the present invention can be used to remove contamination on parts used in the space program, or other high technology areas such as surface science, energy, optics, microelectronics, MEMS, flat-panel processing, solar cells, memory devices, etc. It should be understood that the aforementioned listing of exemplary areas where the present invention may be used is not intended to represent an inclusive listing. Furthermore, it should be appreciated that the wafer as used in the exemplary description herein can be generalized to represent essentially any other structure, such as a substrate, a part, a panel, etc.

While this invention has been described in terms of several embodiments, it will be appreciated that those skilled in the art upon reading the preceding specifications and studying the drawings will realize various alterations, additions, permutations and equivalents thereof. Therefore, it is intended that the present invention includes all such alterations, additions, permutations, and equivalents as fall within the true spirit and scope of the invention. In the claims, elements and/or steps do not imply any particular order of operation, unless explicitly stated in the claims.

What is claimed is:

1. A method for detecting plasma unconfinement in a reaction chamber during a bevel edge cleaning operation, comprising:
    selecting wavelengths associated with expected byproducts of a bevel edge clean process;
    cleaning the bevel edge area of a substrate through a plasma confined to a region proximate to the bevel edge area;
    monitoring the selected wavelengths originating within the chamber during the cleaning for deviation from a wavelength intensity value stored in an external controller, the deviation based on an averaged difference between a maximum wavelength and a minimum wavelength measured over a time period; and
    terminating the cleaning if the deviation from the wavelength intensity value exceeds a target deviation, wherein the deviation from the wavelength intensity value exceeding the target deviation indicates an unconfined condition where the plasma extends outside the region proximate to the bevel edge area.

2. The method of claim 1, wherein the byproducts include silicon fluoride and carbon monoxide.

3. The method of claim 1, wherein the wavelengths are monitored externally through a quartz window of the reaction chamber.

4. The method of claim 1, wherein cleaning the bevel edge area includes striking a plasma proximate to a peripheral edge of the substrate.

5. The method of claim 4, wherein the plasma is a $CF_4$ based plasma.

6. The method of claim 4, wherein an inert gas flows through a center area of the reaction chamber and towards the bevel edge.

7. The method of claim 1, wherein the unconfined condition is a result of an inner region of the substrate being etched.

8. A method for preventing plasma unconfinement from an edge region of a substrate in a reaction chamber during an edge cleaning process, comprising:
    processing a semiconductor substrate in a processing chamber, the processing depositing byproducts on a peripheral edge of the substrate;
    performing an edge cleaning process to remove the deposited byproducts, the edge cleaning process including,
        striking a plasma confined to a peripheral edge region of the substrate;
        monitoring confinement of the plasma to the peripheral edge region, the monitoring performed through a single window embedded into a sidewall of the reaction chamber proximate to the peripheral edge region, the monitoring including,
            tracking a wavelength signal originated within the chamber during the edge cleaning process; and
            determining whether the plasma remains confined to the peripheral edge region based on fluctuation of an averaged difference between a maximum wavelength and a minimum wavelength measured over a time period of the tracked wavelength signal relative to a wavelength intensity value stored in an external controller.

9. The method of claim 8, wherein the byproducts include silicon fluoride and carbon monoxide.

10. The method of claim 8, wherein the wavelength signal is monitored internally within the chamber through an optical emission spectrometer sensor integrated into the reaction chamber.

11. The method of claim 8, wherein the process chamber is an etch chamber.

12. The method of claim 8, wherein the plasma is a $CF_4$ based plasma.

13. The method of claim 8, wherein an inert gas flows through a center area of the reaction chamber and towards the bevel edge during the edge cleaning process.

14. The method of claim 8, wherein determining whether the plasma remains confined based on fluctuation of the tracked wavelength signal includes,
   tracking deviation of the wavelength signal over a time period;
   identifying the maximum wavelength, the minimum wavelength and an average wavelength during the time period.

15. The method of claim 14, further comprising:
   subtracting the minimum wavelength from the maximum wavelength and dividing a result by the average wavelength; and
   comparing a result of the dividing to a threshold value to determine whether the plasma is confined for the time period.

16. The method of claim 15, wherein if the result of the dividing is greater than the threshold value then the edge cleaning process is terminated.

17. The method of claim 8, wherein fluctuation of the tracked wavelength signal is a result of an inner region of the substrate being etched.

18. A method for detecting plasma unconfinement in a reaction chamber during a bevel edge cleaning operation, comprising:
   selecting wavelengths associated with expected byproducts of a bevel edge clean process;
   cleaning the bevel edge area of a substrate through a plasma confined to a region proximate to the bevel edge area;
   monitoring the selected wavelengths originating within the chamber during the cleaning for deviation from a wavelength intensity value stored in an external controller, the deviation based on a ratio of a difference and an average wavelength, the difference between a maximum wavelength and a minimum wavelength, the maximum wavelength, the minimum wavelength, and the average wavelength measured over a time period; and
   terminating the cleaning if the deviation from the wavelength intensity value exceeds a target deviation, wherein the deviation from the wavelength intensity value exceeding the target deviation indicates an unconfined condition where the plasma extends outside the region proximate to the bevel edge area.

* * * * *